United States Patent
Vitek et al.

(10) Patent No.: US 10,449,395 B2
(45) Date of Patent: Oct. 22, 2019

(54) RIB IDENTIFICATION FOR TRANSCOSTAL FOCUSED ULTRASOUND SURGERY

(75) Inventors: Shuki Vitek, Haifa (IL); Yoav Medan, Haifa (IL); Yoav Levy, Hinanit (IL)

(73) Assignee: INSIGHTEC, LTD., Tirat Carmel (IL)

( * ) Notice: Subject to any disclaimer, the term of this patent is extended or adjusted under 35 U.S.C. 154(b) by 908 days.

(21) Appl. No.: 13/323,070

(22) Filed: Dec. 12, 2011

(65) Prior Publication Data

US 2013/0150756 A1    Jun. 13, 2013

(51) Int. Cl.
| | |
|---|---|
| *A61N 7/02* | (2006.01) |
| *A61B 8/08* | (2006.01) |
| *A61B 8/00* | (2006.01) |
| *A61B 5/055* | (2006.01) |
| *G01R 33/48* | (2006.01) |
| *A61B 5/113* | (2006.01) |
| *A61B 5/00* | (2006.01) |
| *A61N 7/00* | (2006.01) |
| *A61B 90/00* | (2016.01) |

(52) U.S. Cl.
CPC ............... *A61N 7/02* (2013.01); *A61B 5/055* (2013.01); *A61B 8/0875* (2013.01); *A61B 8/4416* (2013.01); *A61B 8/485* (2013.01); *A61B 8/5207* (2013.01); *G01R 33/4814* (2013.01); *A61B 5/0035* (2013.01); *A61B 5/113* (2013.01); *A61B 5/4836* (2013.01); *A61B 8/4483* (2013.01); *A61B 2090/374* (2016.02); *A61B 2090/378* (2016.02); *A61N 2007/0052* (2013.01); *A61N 2007/0078* (2013.01); *A61N 2007/0095* (2013.01); *A61N 2007/027* (2013.01)

(58) Field of Classification Search
CPC ........ A61B 2090/374; A61B 2090/378; A61B 5/0035; A61B 5/055; A61B 5/113; A61B 5/4836; A61B 8/0875; A61B 8/4416; A61B 8/4483; A61B 8/485; A61B 8/5207; A61N 2007/0052; A61N 2007/0078; A61N 2007/0095; A61N 2007/027; A61N 7/02; G01R 33/4814
See application file for complete search history.

(56) References Cited

U.S. PATENT DOCUMENTS

| | | |
|---|---|---|
| 4,233,988 A | 11/1980 | Dick et al. |
| 4,509,526 A | 4/1985 | Barnes et al. |

(Continued)

FOREIGN PATENT DOCUMENTS

| | | | |
|---|---|---|---|
| EP | 1 964 518 | * | 9/2008 |
| WO | WO-08/152555 | | 6/2008 |

(Continued)

OTHER PUBLICATIONS

Tanter et al., "Compensating for bone interfaces and respiratory motion in high-intensity focused ultrasound", Int. J Hyperthermia, Mar. 2007, pp. 141-151.*

(Continued)

*Primary Examiner* — Christopher L Cook
(74) *Attorney, Agent, or Firm* — Morgan, Lewis & Bockius LLP

(57) ABSTRACT

A method for transcostal ultrasound treatment of tissues includes determining rib locations, e.g., based on ultrasound reflections off the ribs or acoustic radiation force signals, and transcostally focusing ultrasound into the tissue while minimizing damage to the ribs.

17 Claims, 14 Drawing Sheets

(56) References Cited

U.S. PATENT DOCUMENTS

| | | |
|---|---|---|
| 4,858,597 A | 8/1989 | Kurtze et al. |
| 4,865,042 A | 9/1989 | Umemura et al. |
| 4,873,869 A | 10/1989 | Fink |
| 4,955,366 A | 9/1990 | Uchiyama et al. |
| 4,958,639 A | 9/1990 | Uchiyama et al. |
| 5,111,822 A | 5/1992 | Dory |
| 5,247,935 A | 9/1993 | Cline et al. |
| 5,275,165 A | 1/1994 | Ettinger et al. |
| 5,291,890 A | 3/1994 | Cline et al. |
| 5,307,812 A | 5/1994 | Hardy et al. |
| 5,323,779 A | 6/1994 | Hardy et al. |
| 5,327,884 A | 7/1994 | Hardy et al. |
| 5,368,031 A | 11/1994 | Cline et al. |
| 5,368,032 A | 11/1994 | Cline et al. |
| 5,435,304 A | 7/1995 | Oppelt et al. |
| 5,443,068 A | 8/1995 | Cline et al. |
| 5,485,839 A | 1/1996 | Aida et al. |
| 5,490,840 A | 2/1996 | Uzgiris et al. |
| 5,520,188 A | 5/1996 | Hennige et al. |
| 5,526,814 A | 6/1996 | Cline et al. |
| 5,526,815 A | 6/1996 | Granz et al. |
| 5,590,657 A | 1/1997 | Cain et al. |
| 5,613,940 A | 3/1997 | Romano |
| 5,668,888 A | 9/1997 | Doi et al. |
| 5,711,300 A | 1/1998 | Schneider et al. |
| 5,769,790 A | 6/1998 | Watkins et al. |
| 5,788,665 A | 8/1998 | Sekins |
| 5,844,140 A | 12/1998 | Seale et al. |
| 5,873,845 A | 2/1999 | Cline et al. |
| 5,897,495 A | 4/1999 | Aida et al. |
| 5,984,881 A | 11/1999 | Ishibashi et al. |
| 6,042,556 A | 3/2000 | Beach et al. |
| 6,134,464 A | 10/2000 | Tan et al. |
| 6,182,494 B1 | 2/2001 | Reed et al. |
| 6,217,508 B1 | 4/2001 | Ball et al. |
| 6,368,281 B1 | 4/2002 | Solomon et al. |
| 6,543,272 B1 | 4/2003 | Vitek |
| 6,594,378 B1 | 7/2003 | Li et al. |
| 6,666,833 B1 | 12/2003 | Friedman et al. |
| 6,719,696 B2 * | 4/2004 | Stergiopoulos et al. ..... 600/443 |
| 6,724,925 B2 | 4/2004 | Armato, III et al. |
| 6,748,257 B2 | 6/2004 | Ozaki |
| 7,117,026 B2 | 10/2006 | Shao et al. |
| 7,175,596 B2 | 2/2007 | Vitek et al. |
| 7,344,509 B2 | 3/2008 | Hynynen et al. |
| 7,672,493 B2 | 3/2010 | Qing et al. |
| 2001/0056230 A1 | 12/2001 | Barak et al. |
| 2003/0083597 A1 | 5/2003 | Vitek et al. |
| 2003/0187357 A1* | 10/2003 | Richard ......................... 600/437 |
| 2004/0097806 A1* | 5/2004 | Hunter et al. ................. 600/434 |
| 2006/0224062 A1 | 10/2006 | Aggarwal et al. |
| 2007/0038058 A1* | 2/2007 | West et al. ..................... 600/407 |
| 2007/0086639 A1 | 4/2007 | Sakaida |
| 2007/0223800 A1 | 9/2007 | Guehring |
| 2007/0260137 A1 | 11/2007 | Sato et al. |
| 2008/0107318 A1 | 5/2008 | Kiraly |
| 2008/0137482 A1* | 6/2008 | Kang et al. .................... 367/103 |
| 2008/0200806 A1* | 8/2008 | Liu et al. ....................... 600/439 |
| 2008/0285831 A1 | 11/2008 | Kirchberg et al. |
| 2008/0317322 A1 | 12/2008 | Acharyya et al. |
| 2008/0319375 A1 | 12/2008 | Hardy |
| 2009/0003672 A1 | 1/2009 | Maier et al. |
| 2009/0112132 A1* | 4/2009 | Chang et al. ...................... 601/3 |
| 2010/0030076 A1* | 2/2010 | Vortman et al. .............. 600/439 |
| 2010/0128953 A1 | 5/2010 | Ostrovsky-Berman |
| 2010/0174185 A1 | 7/2010 | Wang et al. |
| 2010/0322493 A1* | 12/2010 | Wei et al. ...................... 382/128 |
| 2011/0144462 A1* | 6/2011 | Lifsitz .................. A61B 5/0059 600/336 |
| 2012/0002840 A1* | 1/2012 | Linnenbank ............. G06K 9/32 382/103 |
| 2012/0136236 A1 | 5/2012 | Roberts |
| 2013/0035582 A1 | 2/2013 | Radulescu et al. |
| 2013/0131494 A1 | 5/2013 | Salomir et al. |
| 2013/0150704 A1 | 6/2013 | Vitek et al. |

FOREIGN PATENT DOCUMENTS

| | | |
|---|---|---|
| WO | WO-10/059056 | 5/2010 |
| WO | WO-10/083415 | 7/2010 |

OTHER PUBLICATIONS

Khokhlova et al., "Focus Splitting Associated with Propagation of Focused Ultrasound Through the Rib Cage", NIH Public Access, Sep. 2010, pp. 1-18.*

Aubry et al., "Transcostal High-Intensity-Focused Ultrasound: Ex Vivo Adaptive Focusing Feasibility Study," retrieved from the internet: http://www.ncbi.nlm.nih.gov/pmc/articles/pmc3021953 (Jan. 2011).

Yoganandan et al., "Optimal Sensor Positioning to Track Rib Deflections From an Optical System in the Hybrid III Dummy," retrieved from the internet: http://www.ncbi.nlm.nih.gov/pubmed/19746314 (Oct. 2009).

Quesson et al., "A Method for MRI Guidance of Intercostal High Intensity Focused Ultrasound Ablation in the Liver," retrieved from the internet: http://www.ncbi.nlm.nih.gov/pubmed/20632565 (Jun. 2010).

Bobkova et al., "Focusing of High-Intensity Ultrasound Through the Rib Cage Using a Therapeutic Random Phased Array," retrieved from the internet: http://www.umbjournal.org/article/s0301-5629(10)00117-1/abstract (Jun. 2010).

Ishikawa et al., "The Ribs: Anatomic and Radiologic Considerations," retrieved from the internet: http://radiographics.rsna.org/content/19/1/105.long (Jan. 1999).

Mitton et al., "3D Reconstruction of the Ribs From Lateral and Frontal X-Rays in Comparison to 3D CT-Scan Reconstruction," retrieved from the internet: http://www.sciencedirect.com/science/article/pii/S0021929007004241 (Sep. 2007).

Botros et al., "A Hybrid Computational Model for Ultrasound Phased-Array Heating in Presence of Strongly Scattering Obstacles," retrieved from the internet: http://www.ncbi.nlm.nih.gov/pmc/articles/PMC2844506/ (Nov. 1997).

Schafer et al., "Propagation Through Inhomogeneous Media Using the Angular Spectrum Method," IEEE Ultrasonics Symposium, pp. 943-946 (1987).

PCT International Application No. PCT/IB2002/05799, International Search Report and Written Opinion dated Jun. 2, 2003, 10 pages.

Cain et al., "Concentric-Ring and Sector-Vortex Phased-Array Applicators for Ultrasound Hyperthermia", IEEE Transactions on Microwave Theory and Techniques, vol. 34, No. 5, May 1986, pp. 542-551.

Cline et al., "Focused US System for MR Imaging-Guide Tumor Ablation", Radiology, vol. 194, No. 3, Mar. 1995, pp. 731-738.

Fjield et al., "The Combined Concentric-Ring and Sector-Vortex Phased Array for MRI Guided Ultrasound Surgery", IEEE Transactions on Ultrasonics, Ferroelectrics and Frequency Control, vol. 44, No. 5, Sep. 1997, pp. 1157-1167.

Manke et al., "Novel Perspective Respiratory Motion Correction Approach for Free-Breathing Coronary MR Angiography using a Patient-Adapted Affine Motion Model", Magnetic Resonance in Medicine, vol. 50, 2003, pp. 122-131.

McDannold et al., "MRI Evaluation of Thermal Ablation of Tumors with Focused Ultrasound", Journal of Magnetic Resonance Imaging, vol. 8, No. 1, Jan./Feb. 1998, pp. 91-100.

Odegaard, Lars A., "Using Signals Scattered From Diffuse Inhomogeneities to Correct for Phase Aberrations Caused by a Phase-Screen Far From the Transducer", 1995 IEEE Ultrasonics Symposium, Jul. 11, 1995, pp. 1443-1447.

Quesson et al., "A Method for MRI Guidance of Intercostal High Intensity Focused Ultrasound Ablation of the Liver", Med Phys, vol. 37, Jun. 2010, pp. 2533-2540.

Staal et al., "Automatic Rib Segmentatioin and Labelling in Computed Tomography Scans Using General Framework for Detection,

(56) References Cited

OTHER PUBLICATIONS

Recognition and Segmentation of Objects in Volumetric Data", Medical Image Analysis, vol. 11, 2007, pp. 35-46.

* cited by examiner

RIB IDENTIFICATION FOR TRANSCOSTAL FOCUSED ULTRASOUND SURGERY

FIELD OF THE INVENTION

In various embodiments, the present invention relates generally to identifying the rib cage of a patient, and more specifically to preventing damage to the ribs during focused ultrasound (FUS) treatment of visceral tissue.

BACKGROUND

Magnetic resonance imaging (MRI) may be used in conjunction with ultrasound focusing in a variety of medical applications. Ultrasound penetrates well through soft tissues and, due to its short wavelengths, can be focused to spots with dimensions of a few millimeters. As a consequence of these properties, ultrasound can be used for various diagnostic and therapeutic medical purposes, including ultrasound imaging and non-invasive surgery. For example, high-intensity focused ultrasonic waves (typically having a frequency greater than 20 kHz) may be used to therapeutically treat the diseased (e.g., cancerous) tissue without causing significant damage to surrounding healthy tissue.

An ultrasound focusing system generally utilizes an acoustic transducer surface, or an array of transducer surfaces, to generate an ultrasound beam. The transducer may be geometrically shaped and positioned such that the ultrasonic energy is focused at a "focal zone" corresponding to the target tissue mass within the patient. During wave propagation through the tissue, a portion of the ultrasound energy is absorbed, leading to increased temperature and eventually to cellular necrosis—preferably at the target tissue mass in the focal zone. The size and length of the focal zone generally depend on the ultrasound frequency, the focal depth, and the aperture size of the transducer. The individual surfaces, or "elements," of the transducer array are typically individually controllable, i.e., their phases and/or amplitudes can be set independently of one another, allowing the beam to be steered in a desired direction and focused at a desired distance and the focal zone properties to be shaped as needed. Thus, the focal zone can be rapidly displaced and/or reshaped by independently adjusting the amplitudes and phases of the electrical signal input into the transducer elements.

In medical applications, the target location of the ultrasound focus is often determined using MRI. Generally, an MRI system, as depicted in FIG. 1A, includes a static-field magnet 102, one or more gradient-field coils 104, a radio-frequency (RF) transmitter 106, and an RF receiver (not shown). (In some embodiments, the same device is used alternately as RF transmitter or receiver.) The magnet includes a region 108 for receiving a patient 110 therein, and provides a static, relatively homogeneous magnetic field over the patient. The gradient-field coils generate magnetic field gradients that vary the static magnetic field. The RF transmitter 106 transmits RF pulse sequences over the patient to cause the patient's tissues to emit magnetic-resonance (MR) response signals. Raw MR response signals are sensed by the RF receiver and then passed to a computation unit 112 that computes an MR image, which may then be displayed to the user. MRI images provide radiologists and physicians with a visual contrast between different tissues and detailed internal views of a patient's anatomy that cannot be visualized with conventional x-ray technology.

The MRI system may be used to plan a procedure, for example, a surgical or minimally invasive procedure, such as a focused ultrasound ablation procedure, before its execution. A patient may initially be scanned in an MRI system in preparation for a procedure to locate a target tissue region and/or to plan a trajectory between an entry point (or region) and the target tissue region. Once the target tissue region has been identified, MRI may be used during the procedure, for example, to image the tissue region and/or to guide the trajectory of an external ultrasound beam to the target tissue region being treated. For example, using displayed images of an internal body region, a treatment boundary can be defined around the target tissue mass, and obstacle boundaries can be defined around tissue that should not be exposed to the ultrasound energy beam or whose exposure to ultrasound should be controlled and limited. The ultrasound transducer can then be operated based on these defined boundaries. These methods are generally referred to as magnetic-resonance-guided focused ultrasound (MRgFUS) methods.

While MRgFUS methods have been used effectively for the treatment of, for example, brain tumors and breast cancer, they still face significant challenges when applied to transcostal procedures, i.e., the treatment of visceral organs (such as the liver) that lie behind the rib cage. Ultrasound penetration of the rib cage does, in general, not only risk disruption of the acoustic beam profile by the ribs (resulting in diminished treatment efficacy for the target organ) and the formation of acoustic hot spots, but also undesired damage to the ribs. The location of the ribs, therefore, needs to be taken into account during treatment planning In rib images obtained using current conventional tomography (e.g., MRI), however, the boundaries of the ribs are usually difficult to identify due to low signal levels from the cortex and partial-volume effects, i.e., the presence of bone marrow and soft tissue in the same volumetric pixel (i.e., voxel). In addition, the use of an MRI apparatus for imaging places considerable constraints on the type of equipment that can be used in the system. For example, equipment constructed from ferromagnetic materials (such as motors, which may be desirable to use in a positioning system for the ultrasound transducer) cannot be used near an MRI system since the large magnetic fields generated by the MRI system will physically attract the magnetic equipment, and conductive materials can disturb and distort the RF electromagnetic fields necessary for resonance imaging.

Moreover, motion of the rib cage, e.g., during respiration, complicates rib localization. To precisely locate the ribs with respect to the ultrasonic transducer throughout the treatment, it may be necessary to track the rib cage continuously, and to stop the treatment process to correct for any misalignment due to a displacement of the rib cage and/or the internal organ to be treated. This results in significant inefficiencies in the treatment process and may generate significant delays.

Accordingly, there is a need for alternative methods of determining and tracking rib locations in an ultrasound treatment setting.

SUMMARY

The present invention provides systems and methods for utilizing low-energy ultrasound pulses (i.e., pulsed ultrasound that does little or no damage) to identify and locate the rib cage. The rib cage may be irradiated with low-energy ultrasound waves or scanned with a low-energy ultrasound focus, and reflections off the ribs may be analyzed to determine the rib locations. Images generated from the reflected low-energy ultrasound waves have good resolution, so the location of the rib cage, identified utilizing the low-energy ultrasound waves, can be used prior to focused-ultrasound treatment to plan a therapeutic procedure, and/or during treatment to guide the ultrasound focus. Acoustic hot spots resulting from ultrasound interaction with the rib cage can be predicted and avoided or minimized (e.g., by beam forming). Additionally, movements of the rib cage during the treatment can be precisely and timely tracked by analyzing the reflected ultrasound waves from the ribs without stopping the procedure. The approach described herein can be implemented even in the presence of devices made of ferromagnetic or conductive materials, and thus provides more flexibility for the treatment apparatus.

In an alternative approach, low-energy pulsed ultrasound is used to induce displacement of the soft tissue between the ribs while having no significant effect on the ribs. For example, one or more line foci may be applied at particular locations across (i.e., perpendicular to) the ribs, or a point or line focus may be scanned across the rib cage. The displacement of the soft tissue can be imaged with a suitable MRI sequence. Alternatively, ultrasound elastography may be used to image the acoustically stimulated tissue. This technique provides a complementary method to determine the location of the rib cage.

Accordingly, in one aspect, the invention pertains to a method for transcostal ultrasound treatment of target tissue. The method includes: (i) determining rib locations based on ultrasound reflections off the ribs, and (ii) based on the determined rib locations, treating the target tissue by focusing ultrasound into the target tissue substantially without damaging the ribs.

In one embodiment, during the treatment, the ultrasound is focused in a pattern (or along a path) that substantially avoids the ribs. Determining the rib locations may include scanning an estimated rib zone with an ultrasound focus and analyzing ultrasound reflections resulting therefrom. In one implementation, analyzing the ultrasound reflections includes associating ribs with reflections above a specified intensity threshold. In various embodiments, the focused-ultrasound pulse energy during scanning is lower than the focused-ultrasound pulse energy during treatment.

In some embodiments, the ultrasound focus is a point focus or a line focus. In one embodiment, multiple portions of the estimated rib zone are scanned in parallel with multiple ultrasound foci. In various implementations, the multiple ultrasound foci are generated by multiple sub-arrays of a phased-array ultrasound transducer.

In various embodiments, determining the rib locations includes irradiating the ribs with ultrasound waves and, based on ultrasound reflections resulting therefrom, volumetrically reconstructing a reflected ultrasound field. The ultrasound waves may be, without limitation, plane waves, omni-directional waves, and/or focused waves. The volumetric reconstruction may utilize time-of-flight correlation, Raleigh integrals, and/or Fast Fourier Transform. Determining the rib locations may involve associating ribs with ultrasound field strengths above a specified intensity threshold.

In some embodiments, determining the rib locations includes modeling the rib locations using at least one parameter, and estimating the parameter(s) based on the ultrasound reflections. Modeling the rib locations may include obtaining geometric data of the ribs by computed tomography, magnetic resonance imaging, ultrasound scans, and/or a generic anatomical model.

In one embodiment, the method further includes tracking rib motion during treatment based, at least in part, on changes in the ultrasound reflections. In one implementation, the rib motion tracking is further based on a computational model of the rib motion.

The method may, further, include validating ultrasound beam apodization prior to treatment based on ultrasound reflections.

In a second aspect, the invention relates to a system for transcostal ultrasound treatment of target tissue. The system includes: (a) a transducer array, including a plurality of transducer elements, for transmitting acoustic energy to the target tissue and receiving reflections thereof, (b) a processor coupled to the array for determining locations of ribs based on the acoustic reflections from the target tissue, and (c) a controller for driving the transducer elements to acoustically treat the target tissue based at least in part on the locations of the ribs.

In a third aspect, the invention relates to a method for transcostal ultrasound treatment of target tissue. The method includes: (i) determining rib locations based on imaging (e.g., acoustic radiation force impulse imaging) of tissue displacements between the ribs, and (ii) based on the determined rib locations, treating the target tissue by focusing ultrasound into the target tissue substantially without damaging the ribs. In various embodiments, the ultrasound is focused along a path that substantially avoids the ribs.

In various embodiments, determining the rib locations includes creating an ultrasound focus across the ribs, and analyzing tissue displacements resulting therefrom, e.g., by associating ribs with tissue displacements below a specified threshold. In one implementation, multiple ultrasound foci are created at different locations along an elongated dimension of the ribs.

In one embodiment, a focused ultrasound pulse energy during determination of the rib locations is lower than a focused-ultrasound pulse energy during treatment. Determining the rib locations may include scanning an estimated rib zone with an ultrasound focus (e.g., a point or line focus). In some implementations, multiple portions across the ribs are scanned in parallel with multiple ultrasound foci.

In some embodiments, the rib locations are determined based on magnetic-resonance acoustic radiation force impulse imaging. In other embodiments, the rib locations are determined based on ultrasound-based acoustic radiation force impulse imaging.

In a fourth aspect, the invention relates to a system for transcostal ultrasound treatment of target tissue. The system includes: (a) a transducer array, including a plurality of transducer elements, for transmitting acoustic energy to the target tissue, (b) an imaging unit for capturing at least one of displacement or a mechanical property (e.g., the elasticity) of target tissue resulting from the acoustic energy transmitted thereon, (c) a processor, responsive to the imaging unit, for determining locations of ribs based on the displacement of the target tissue, and (d) a controller for driving the transducer elements to acoustically treat the target tissue based at least in part on the locations of the ribs. In some embodiments, the imaging unit includes or consists of an MRI unit and/or an ultrasound detector.

In general, as used herein, the term "substantially" means ±10% (e.g., by weight or by volume), and in some embodiments, ±5%. The term "substantially without damaging" means with sufficiently minimal tissue damage as to be considered clinically insignificant by those of skill in the art. For example, temporary bone heating that is painful, but which does not harm the ribs permanently, is "substantially without damage." In general, the threshold for the application of ultrasound "substantially without damaging" tissue (such as the ribs) can be quantified in terms of the maximum clinically tolerable temperature (or thermal dose) per organ, as determined, e.g., by the treating physician on a case-by-case basis.

The terms "point focus" and "line focus," as used herein, do not refer to points and lines in the strict mathematical sense, but to focus shapes that approximates a point or line, respectively. Thus, the intensity distribution of a point focus (which may, for example, take the shape of a two-dimensional Gaussian distribution) may be characterized by half-widths in both dimensions of the focal plane on the order of a few acoustic wavelengths, whereas the intensity distribution of a line focus (which may, for example, have a one-dimensional Gaussian profile perpendicular to the line) is extended along the direction of the line, but may have a half-width perpendicular thereto on the order of only a few acoustic wavelengths.

These and other advantages and features of the present invention will become more apparent from the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Ultrasound Systems and Techniques

Figure 1A:
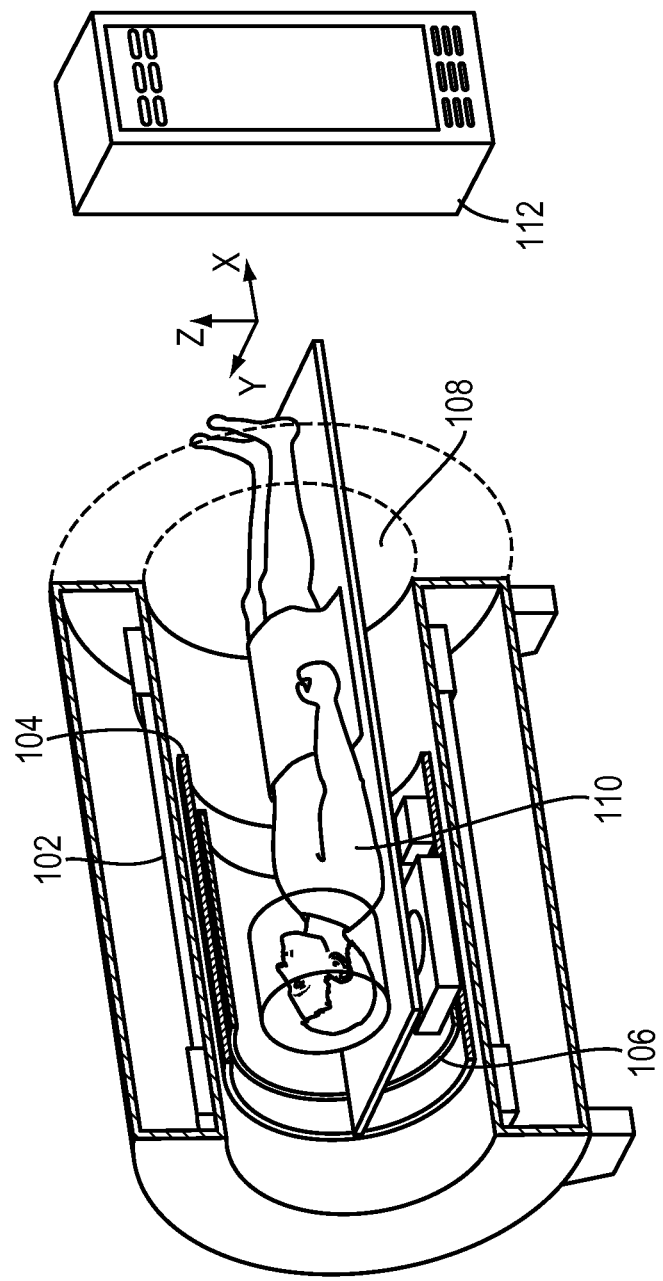
FIG. 1A schematically depicts an exemplary MRI system.
Figure 1B:
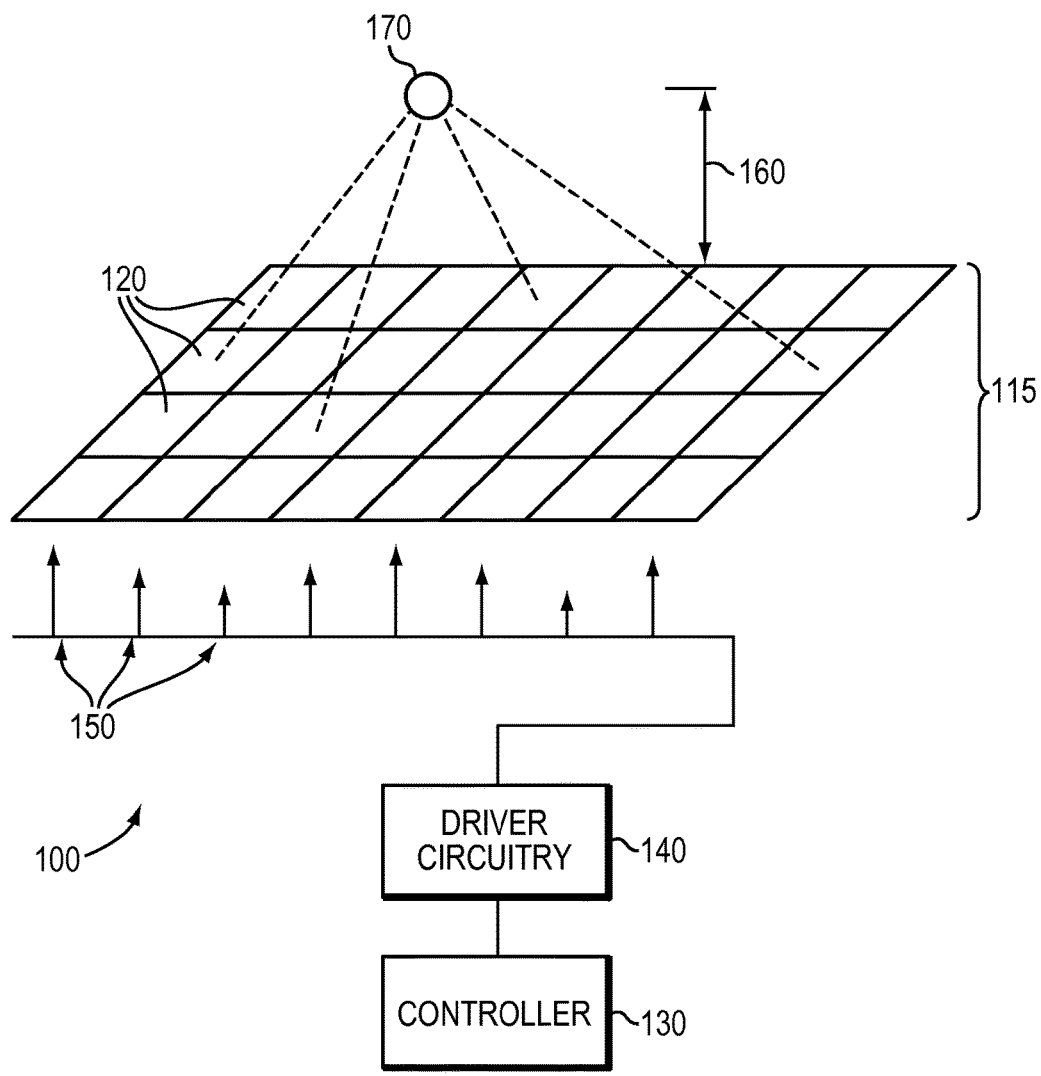
FIG. 1B schematically depicts an exemplary focused ultrasound system.

FIG. 1B depicts an exemplary focused ultrasound system 100 in accordance with embodiments of the present invention, although alternative systems with similar functionality are also within the scope of the invention. As shown, an ultrasound transducer matrix 115 used as a transmit-receive probe is formed by transducer elements 120 made of piezoelectric material. A controller 130 coupled to drive circuitry 140 controls several aspects of drive signals 150 generated by the drive circuitry 140, such as the frequency, phase, and amplitude. For example, the controller 130 may control the amplitude of the drive signals 150 to control the energy of the acoustic field delivered by the transducer matrix 110. In addition, the controller 130 may control the relative phases and amplitudes of the signals driving the transducer elements 120. By shifting the phases between the transducer elements 120, a focal distance 160 (i.e., the distance from the transducer 110 to the center of the focal zone 170), and the size, shape, and lateral position of the focal zone 170 may be adjusted. By changing the relative phase settings in time, the array matrix can be used to provide a two- or three-dimensional scan and, thus, to obtain more detailed information about the target at the focal zone.

Figure 2:
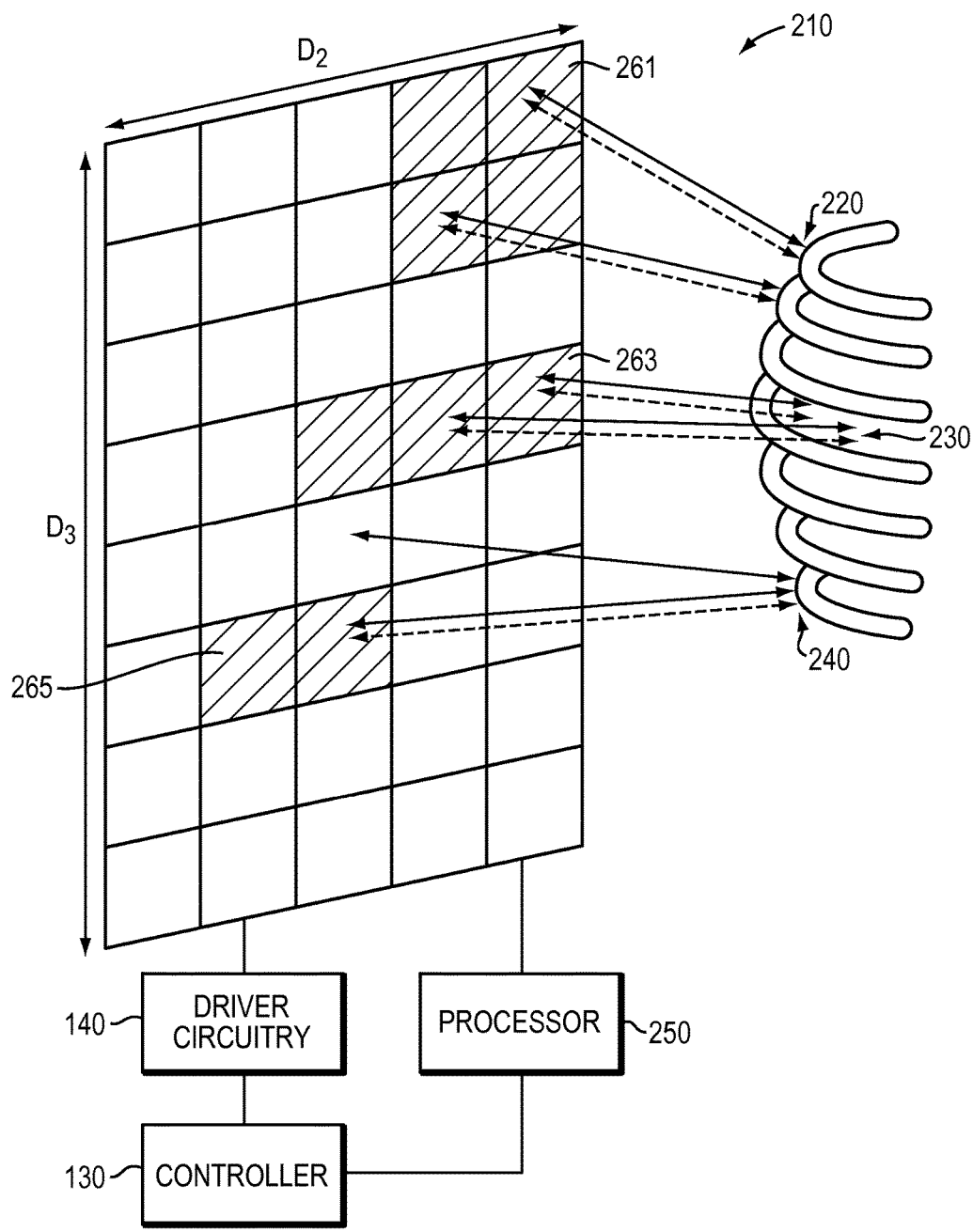
FIG. 2 depicts an ultrasound method of locating the ribs where ultrasound waves are transmitted to the estimated zone of the ribs and the reflected waves are received therefrom.

In a transcostal focused ultrasound treatment procedure, it is useful to identify rib locations to avoid rib damage and treat the tissue more efficiently. In some embodiments, referring to FIG. 2, the phased-array transducer matrix 210 transmits low-power ultrasound waves to the estimated zone of the ribs 220, 230, and 240 and receives the waves reflected therefrom. The transducer may possess both transmit and receive capabilities. In one embodiment, each transducer element alternates between transmitting and receiving ultrasound waves. In another embodiment, some transducer elements transmit the ultrasound waves while other transducer elements receive the reflected waves at the same time. The transmit and receive regions of the transducer array may be configured in different patterns and shapes. During the rib-identification procedure, the ultrasound transducer is driven at sufficiently low power such that the emitted ultrasound waves do not cause any significant damage to the ribs. A processor 250 analyzes the measured wave reflection signals, in the manner described below, to obtain information about the transmission and reflection of the ultrasound waves and, thus, about the rib cage. This information is provided to the controller 130, which operates the transducers 150 in accordance therewith. (In some embodiments, the functions of the processor 250 are implemented directly by the controller 130—i.e., by a processor internal to the controller.)

More generally, the controller 130 and the processors 250, 570 (the latter described below) may be implemented in hardware, software or a combination of the two. For embodiments in which the functions are provided as one or more software programs, the programs may be written in any of a number of high level languages such as FORTRAN, PASCAL, JAVA, C, C++, C#, BASIC, various scripting languages, and/or HTML. Additionally, the software can be implemented in an assembly language directed to the microprocessor resident on a target computer. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

In certain embodiments, the rib cage is scanned with a sequence of low-energy ultrasound point foci, or line foci oriented parallel to the ribs. (Alternatively, a point or line focus may be continuously swept across the rib cage.) Since ultrasound waves do not pass well through bone tissues, high reflection occurs when the point or line focus encounters the ribs (see, e.g., zones 220 and 240), while the reflection is significantly less when the focus falls between the ribs (see, e.g., zone 230). Based on the detected reflection signal from each focus in the sequence, the ribs may be located by thresholding (e.g., binary intensity thresholding). The threshold may be determined, for example, as the mean intensity value plus one standard deviation. Reflected waves with intensities above the threshold are considered to come from the rib cage while reflected waves with intensities below the threshold are considered to come from soft tissue in the gaps between the ribs.

Once the rib locations have been identified based on the information from reflected low-energy ultrasound, high-energy ultrasound pulses may be focused into the target tissue behind the rib cage along a path that substantially avoids the ribs and, thus, causes little or no damage to the ribs. This can be accomplished, for example, by turning off the transducer elements that are positioned directly in front of the ribs; turning off (or reducing the amplitude of) transducer elements whose waves are prevented, by interjacent ribs, from reaching the target; iteratively identifying elements to be turned off based on measured or simulated acoustic fields at the rib cage and/or target; using holographic techniques to construct an acoustic beam that has minimal intensity at the ribs; or a combination of the preceding beam forming methods.

Typically, the distance D1 between the ribs and the transducer is short compared with the dimensions D2×D3 of the phased-array ultrasound transducer; therefore, as illustrated, a sub-array (i.e., a contiguous set of a few array elements, e.g., 261, 263, and 265), of the transducer is utilized to detect the rib locations within a portion of the estimated rib zone. Consequently, multiple sub-arrays of a transducer that are far enough apart to not interfere with each other can be used in parallel to generate multiple ultrasound foci on the estimate rib zone. This approach significantly decreases the time to determine the location of the ribs. Alternatively, multiple sub-arrays may emit ultrasound waves in accordance with a "smart" time sequence that specifies the relative timing of sub-array operation; this can also increase the efficiency of detecting the rib locations.

Figure 3:
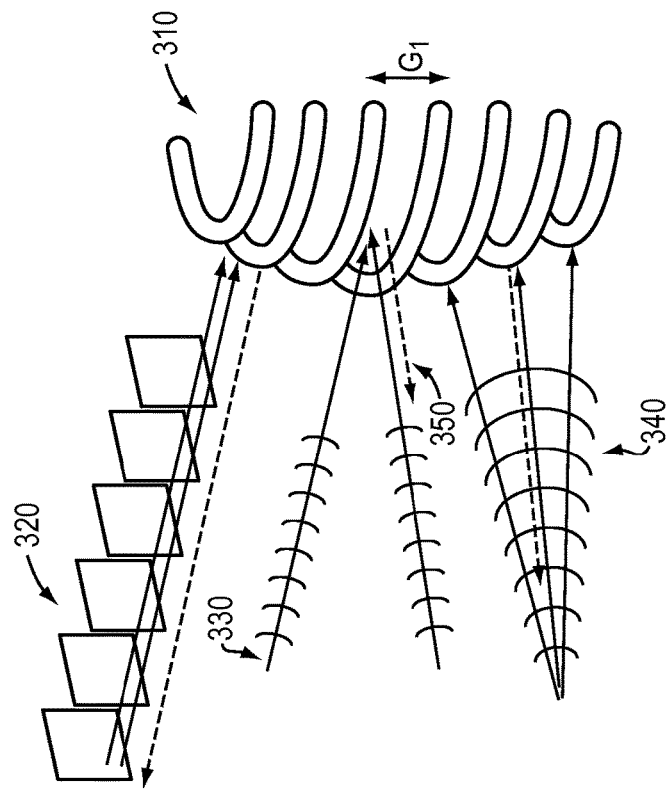
FIG. 3 depicts that ultrasound waves transmitted from the transducer may include plane waveforms, focused waveforms, and omni-directional waveforms.
Figure 3:
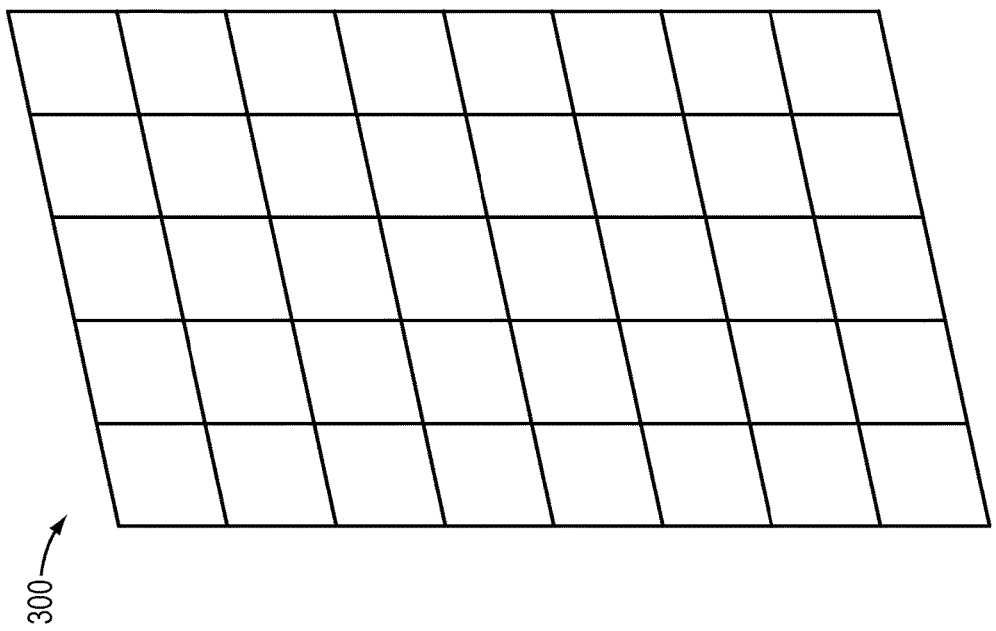

In various embodiments, a portion of the rib cage that spans multiple ribs (e.g., the entire rib cage) is simultaneously irradiated with ultrasound waves, and the rib locations are determined based on a volumetric reconstruction of the reflected ultrasound field. With reference to FIG. 3, ultrasound waves transmitted from the transducer 300 to the estimate rib zones 310 may include plane waveforms 320, focused waveforms 330 (e.g., with a focus position behind the rib cage), and/or omni-directional (e.g., spherical diverging) waveforms 340; however, other waves of arbitrary shape may be used as well. The soft tissues between the ribs can be identified by their significantly lower reflecting field values 350 in a volumetric reconstruction. The reflected ultrasound field strengths above a specified intensity threshold are utilized to define the location of the ribs. In various embodiments, a reconstruction method such as time-of-flight correlation, the Rayleigh integral method, and/or the Fast Fourier Transform (i.e., angular spectrum) method is used for the volumetric reconstruction. Two or more of these methods may be combined to yield the final identification of ribs.

In one embodiment, time-of-flight cross-correlation is used to reconstruct a reflected ultrasound field and, based on the field, characterize the structure of the rib cage. In brief, the acoustic reflection intensity is sampled in time by the individual transducer elements. For each element, different sampling windows (i.e., time intervals) correspond to signals received from different source volume elements (voxels); the applicable window for each voxel can be calculated based on the acoustic time of flight from that voxel to the respective transducer element. The probability of having a strong acoustic reflector (i.e., bone tissue) in a particular voxel is estimated by correlating the signals of the transducer elements within the sampling windows corresponding to that voxel (i.e., by integrating the product of the signals received at the transducer elements, time-shifted by the respective times of flights, over the sampling window).

In another embodiment, the Rayleigh integral is used to reconstruct the reflected ultrasound field. This method is similar to time-of-flight cross-correlation, but also takes the phase of the measured reflection into account. Both time-of-flight cross-correlation and the Rayleigh integral method are well-known to persons of skill in the art, and details can be found in the scientific literature.

Figure 4:
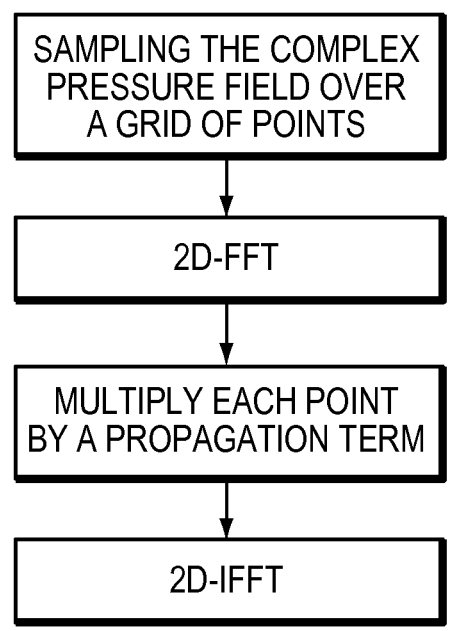
FIG. 4 illustrates the numerical principle for volumetric reconstruction of the reflected acoustic field using the Fast Fourier Transform method.

In one embodiment, a Fast Fourier Transform (FFT) projection method is used to model the reflected acoustic field numerically. The Fast Fourier Transform facilitates rapid reconstruction of the acoustic field reflected from the estimate rib zones. This approach involves expanding the ultrasound field measured at the plane receiving the reflected signals (e.g., at the plane of the transducer) into a summation over an infinite number of plane waves, and yields an acoustic field distribution over the rib cage. The FFT method not only takes into account the phase of the reflected signals, but also utilizes the computational efficiency of FFT to expedite the computation. In one embodiment, numerically modeling the reflected acoustic field involves the following steps, as shown in FIG. 4:

(1) Sampling the pressure field over a grid of points lying in a cross-sectional plane (i.e., the plane receiving the reflected ultrasound waves) within the field at various points in time (each point in time corresponding to a particular time of flight and, thus, a particular slice constituting the source of the pressure field), and converting the measured pressures into complex values (e.g., using quadrature amplitude modulation).

(2) Selecting a plane to be reconstructed (e.g., the plane of the rib cage). (3) Taking the two-dimensional FFT (the 2D-FFT) of the complex signal corresponding to the selected plane. This step decomposes the field into a two-dimensional angular spectrum of component plane waves each traveling in a unique direction.

(4) Multiplying each point in the 2D-FFT by a propagation term which generally depends on the propagation distance and accounts for the phase change that each plane wave undergoes on its journey from the reconstruction plane (e.g., the rib cage) to the measurement plane (where the signal is sampled). Methods for determining the propagation term are generally known to those of skill in the art, and are described, for example, in Schafer et al., "Propagation Through Inhomogeneous Media Using the Angular Spectrum Method," 1987 Ultrasonics Symposium, pp. 943-46, which is hereby incorporated herein by reference in its entirety.

(5) Taking the two-dimensional inverse Fast Fourier Transform (2D-IFFT) of the resulting data set to reconstruct the field over the rib cage (or other selected plane). In case the wave travels through two (or more) media with different acoustic properties, reconstruction is split into two (or more) steps (e.g., such that the first step yields the reconstructed acoustic field at the boundary between the two media, and the second step yields the reconstructed field at the plane of the rib cage).

(6) Volumetric reconstruction from 2D-slices may be accomplished by repeating steps (2)-(5).

In some embodiments, a model describing the rib cage already exists. The model may, for example, be a generic anatomical model, or a model created from a preoperative computed tomography (CT) scan, magnetic resonance imaging (MRI) data, a chest radiograph, an ultrasound scan, or any combination of such data. The model generally includes one or more parameters (e.g., positional parameters of the ribs) whose values may be estimated based on the measured ultrasonic reflection. One parameter-estimation method involves finding the set of values that maximizes the reflection of the ultrasound waves, since higher reflection indicates a larger portion of ultrasound waves interacting with the ribs rather than the tissue in between. This process can be iteratively implemented (that is, the initial parameter values for the next measurement set are determined based on the results of the previous measurements) until the result is satisfactory.

In various embodiments, the motion of the ribs (e.g., due to breathing) is continuously tracked during the therapeutic treatment. The rib locations can be found by continuously following the changes in the acoustic reflection readout maps. Alternatively or additionally, a simple model of the rib cage motion (e.g., a one-dimensional translational model characterizing the motion during the breathing cycle) may be used to track the rib locations. Such a model can be created, for example, by analyzing images taken from the patient before treatment at different stages during the cycle of motion. (Alternatively, a generic model based on the motion cycle for one or more different patients may be used.)

In various embodiments, a treatment plan that avoids damage to the ribs is created prior to the treatment. To verify in a therapeutic setting that the treatment plan results in safe ultrasound levels, ultrasound reflection measurements may be used prior to each sonication. If adjustments are necessary, the signal profile of the transducer elements can be changed deliberately (e.g., by shutting down or reducing the amplitude of individual elements) to optimize beam apodization (i.e., the beam profile resulting from the superposition of the waves emanating the selected transducer elements). The amount of acoustic reflection measured from an acoustic beam with optimal apodization is significantly lower than the amount of reflection measured in a configuration that potentially damages the ribs.

ARFI Imaging Systems and Techniques

ARFI (Acoustic Radiation Force Impulse) imaging techniques generally utilize the mechanical pressure generated by focused ultrasound to cause momentum transfer to and displacements of tissue, which can then be imaged in various ways. For example, in ultrasound-based ARFI imaging, the stiffness of the displaced tissue is imaged with ultrasound (ultrasound elastography). In MR-ARFI imaging, a special MRI pulse sequence is utilized to capture the tissue displacement resulting from the acoustic pressure.

More specifically, in MR-ARFI methods, a displacement-sensitizing magnetic field gradient is generated by gradient coils, which are part of standard MRI systems and are typically located near the cylindrical electromagnet coil that generates the uniform static magnetic field. When the ultrasound pulse is applied in the presence of such gradient, the resulting displacement is directly encoded into the phase of the MR response signal. For example, the gradient coils and transducer may be configured such that the ultrasound pulse pushes tissues near the focus towards regions of the magnetic field with higher field strengths. In response to the resulting change in the magnetic field, the phase of the MR response signal changes proportionally, thereby encoding in the signal the displacement caused by the ultrasound radiation pressure. The level of displacement is proportional to the tissue's mechanical properties (e.g., elasticity). For example, soft tissue displaces more than rigid tissue (e.g., bones) upon applying a force. The marked difference in mechanical properties between different tissues can then be leveraged by MR-ARFI to differentiate between the inter-rib space and the ribs themselves.

Figure 5:
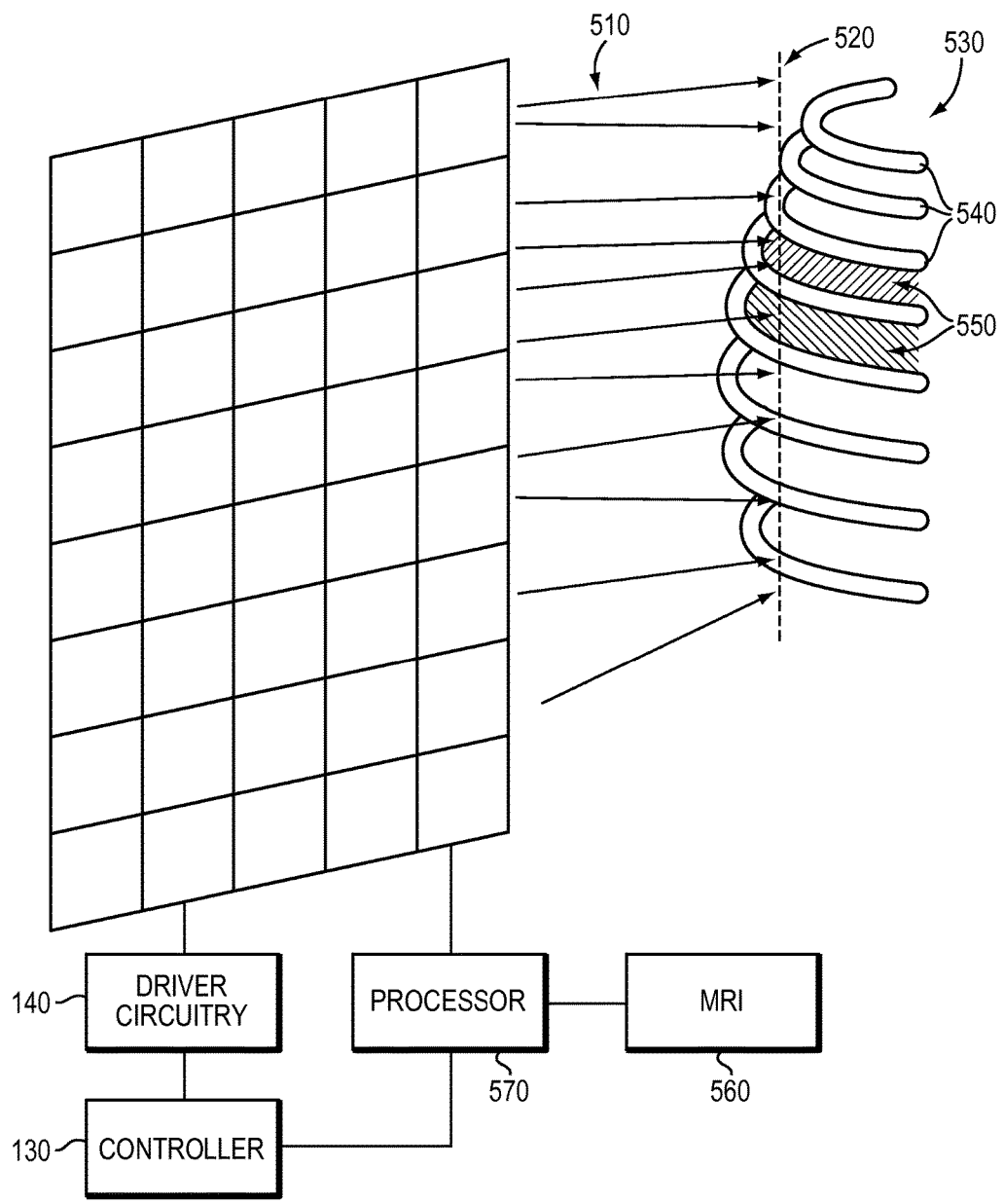
FIG. 5 depicts the MR-ARFI method of locating the ribs where a line focus of the ultrasound waves is applied perpendicularly to the rib cage.

In various embodiments, with reference to FIG. 5, a short, low-energy ultrasound pulse 510 forming a line focus 520 is applied perpendicularly to the rib cage 530, i.e., such that the line focus 520 intersects the ribs 540. The acoustic radiation force generated by the line focus 520 induces tissue displacements of the soft tissues 550 between the ribs 540, which can be imaged using MRI 560, while it does not (or only insignificantly) displace the locations of the ribs 540. The MR image is then analyzed using a processor 570 (which, again, may be incorporated within the controller 130), and the soft tissue 550 between the ribs 540 is identified by the processor where the tissue displacement exceeds a specified threshold. The MR-ARFI technique thus identifies an acoustic window of the rib cage for the subsequent therapeutic-level sonications, which may be crafted using part of the acoustic array to minimize the acoustic energy delivered to the ribs so as to avoid damage to the ribs.

In some embodiments, the MR-ARFI process is repeated several times to map the accessible area for the whole acoustic array; each time, the ultrasound focus is generated at a different position along the ribs. For example, in one implementation, two line foci are utilized to map the rib cage under an assumption of uniform ribs, one at the left edge of the rib cage and one at the right edge of the rib cage. In between the two foci, the location of the ribs is determined by interpolation. Additional foci may be used to improve interpolation and averaging of any errors due to imaging noise.

In certain alternative embodiments, the rib cage is scanned with a series of ultrasound line foci parallel to the ribs (or a series of point foci), such that each focus falls either substantially between the ribs or on the rib. The soft and bone tissues are identified by the processor 770 based on the strength of the MR-ARFI signal associated with each focus position, with inter-ribs space corresponding to MR-ARFI signals exceeding a predetermined threshold. This MR-ARFI embodiment is complementary to the reflection-based ultrasound embodiments described above in that it determines rib locations based on signals originating in the soft tissue between the ribs, rather than based on reflections off the ribs. As in described above with respect to ultrasound reflection methods, multiple foci generated in parallel by different sub-arrays of the transducer, or by sophisticated beam forming, may be used to scan different portions of the rib cage simultaneously.

Once the rib locations have been determined, MR-ARFI may also be used to improve the focus quality and accuracy of the focus position prior to sonicating the visceral tissues at therapeutic ultrasound levels. For example, in an autofocusing procedure, optimal phase settings may be determined by creating an initial focus between the ribs, and successively fine-tuning the phases of all the transducer elements (or groups of transducer elements). The fine-tuning of each element (or group of elements) may be accomplished, for example, by varying the phase of that element (or group of elements) while holding the phases of the other transducer elements constant, and setting the phase of the selected element to a value that optimizes the focus quality as measured with MR-ARFI (e.g., the value that results in the strongest MR-ARFI signal). These steps are repeated for each element (or group of elements) individually. Once the phases have been updated for the entire array, the process may be iteratively repeated until a desired focus quality is achieved.

The rib localization methods described above with reference to MR-ARFI imaging can straightforwardly be adjusted to ultrasound-based ARFI imaging.

MR Imaging Systems and Techniques

Figure 6A:
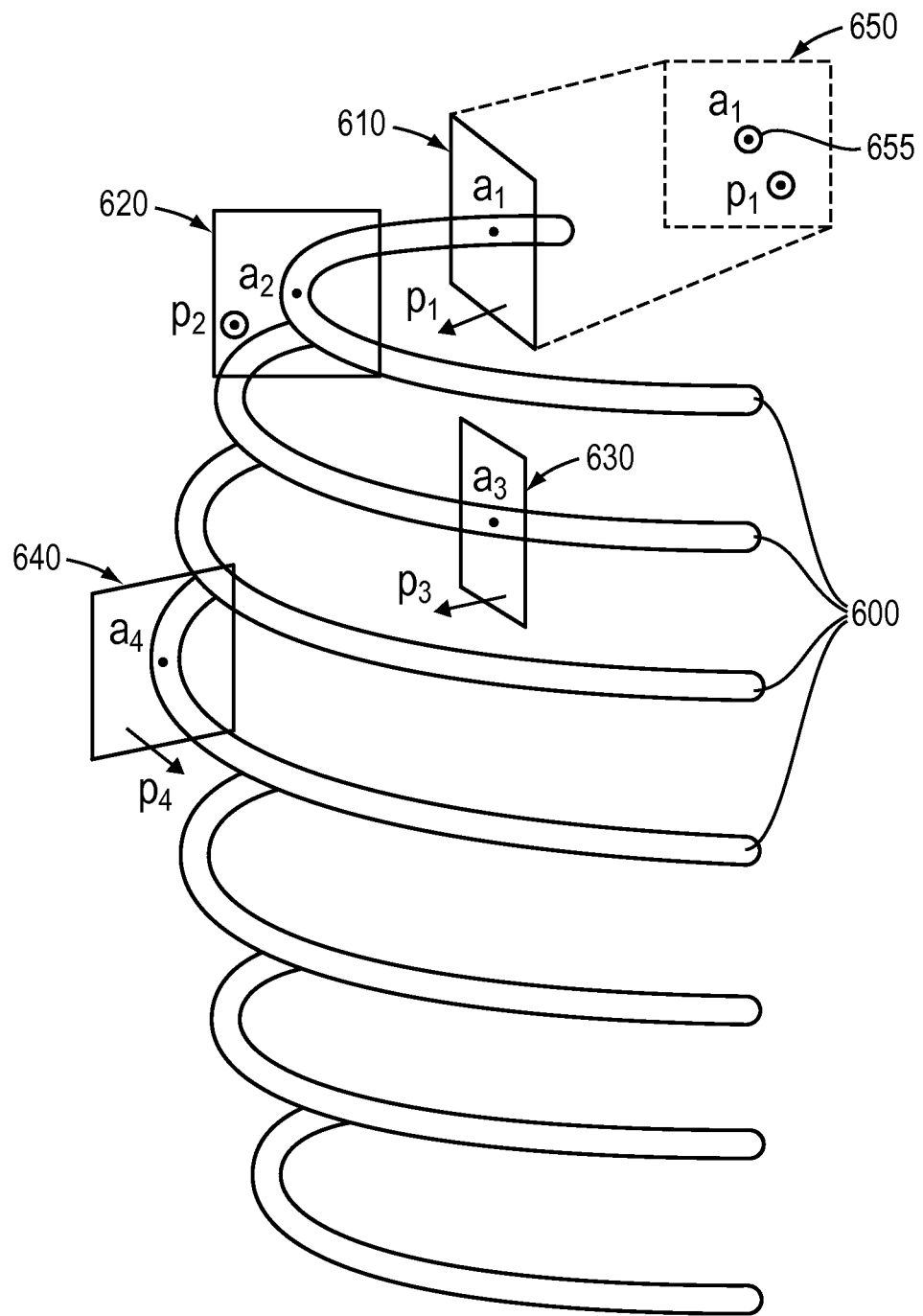
FIG. 6A schematically depicts image slices that are taken perpendicular to the local orientation of the ribs.

In some embodiments, the rib locations are determined from a three-dimensional model of the rib cage that is constructed based on a series of tomographic image slices. The images may be obtained using any of a variety of tomographic imaging modalities, including, e.g., MRI and X-ray-based computer tomography. Whereas conventional tomography utilizes one or more sets of parallel image slices (each set typically being oriented parallel to the sagittal, axial, or coronal plane of the body), various embodiments in accordance with the present invention build volumetric image data from "oblique" image slices taken at different positions along the ribs with different orientations, i.e., image slices "tailored" to the geometry of the rib cage. In some embodiments, as illustrated in FIG. 6A, the image slices are taken locally perpendicular to the elongated dimension of the ribs 600. For example, images slices of planes 610, 620, 630, and 640 are taken perpendicularly to the orientation of the ribs at positions $a_1$, $a_2$, $a_3$, and $a_4$, respectively. Since the orientation of the ribs varies between locations $a_1$, $a_2$, $a_3$, and $a_4$, the image slices have respective normal vectors $p_1$, $p_2$, $p_3$, and $p_4$ that point in different directions.

In conventional MR (or other tomographic) imaging, thick image slices typically suffer from the partial volume artifact, which is caused by an imaging voxel containing two or more different tissues and thus possessing a signal average of all tissues. An image voxel can contain multiple tissues, despite high in-plane image resolution, if the locations of the tissue boundaries vary with depth within the image slice. This problem is largely avoided with image slices taken perpendicular to the local orientation of the ribs, allowing slices to be quite thick (e.g., 7 mm) without causing partial-volume degradation in the images. An in-plane resolution of about 1 mm or better is generally sufficient to provide a sharp image of the edges between the cortex (which may be rather thin, typically 1 to 2 mm) and the bone marrow on one side of the cortex, and/or the adjacent tissue on the other side.

Within an image 650 taken locally perpendicular to the rib (i.e., a cross-section image), the boundary of the rib can be approximated with an ellipse 655, which can be fully characterized by its width, length, orientation, and center position. The resulting series of characterized ellipses may be used to generate a simple model of the rib cage, as described in more detail below. (In some embodiments, the rib cross sections are modeled by other geometric approximations, e.g., rectangles.)

Figure 6B:
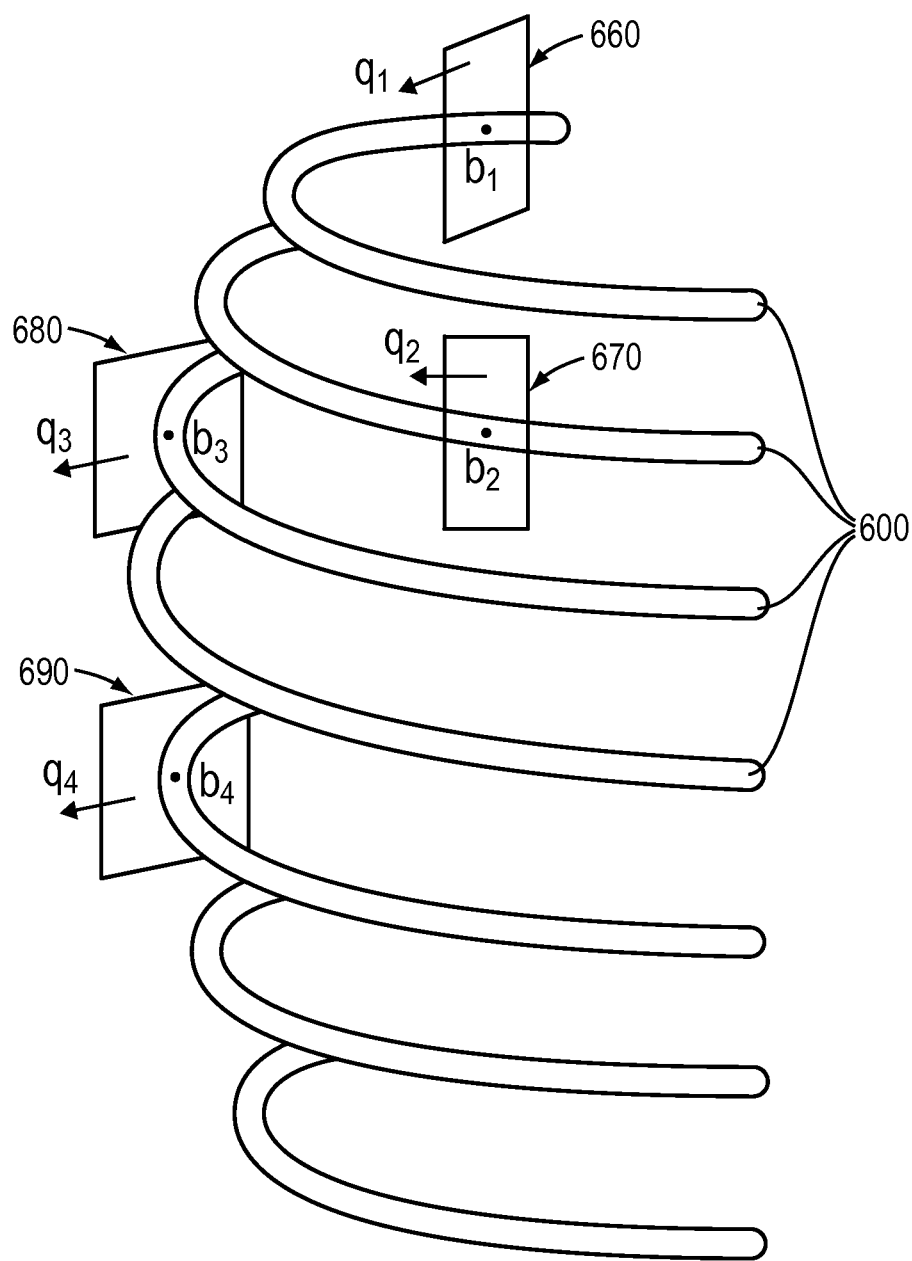
FIG. 6B schematically depicts image slices that are taken parallel to the local orientation of the ribs.

In some embodiments, referring to FIG. 6B, image slices are taken locally parallel to the elongated dimension of the rib. For example, the image slices of planes 660, 670, 680, and 690 are taken parallel to the orientation of the ribs at locations $b_1$, $b_2$, $b_3$, and $b_4$, respectively. Again, since the rib orientation varies between these locations, the respective image slices have different orientations (characterized by normal vectors $q_1$, $q_2$, $q_3$, and $q_4$ pointing in different directions) as well.

Figure 7:
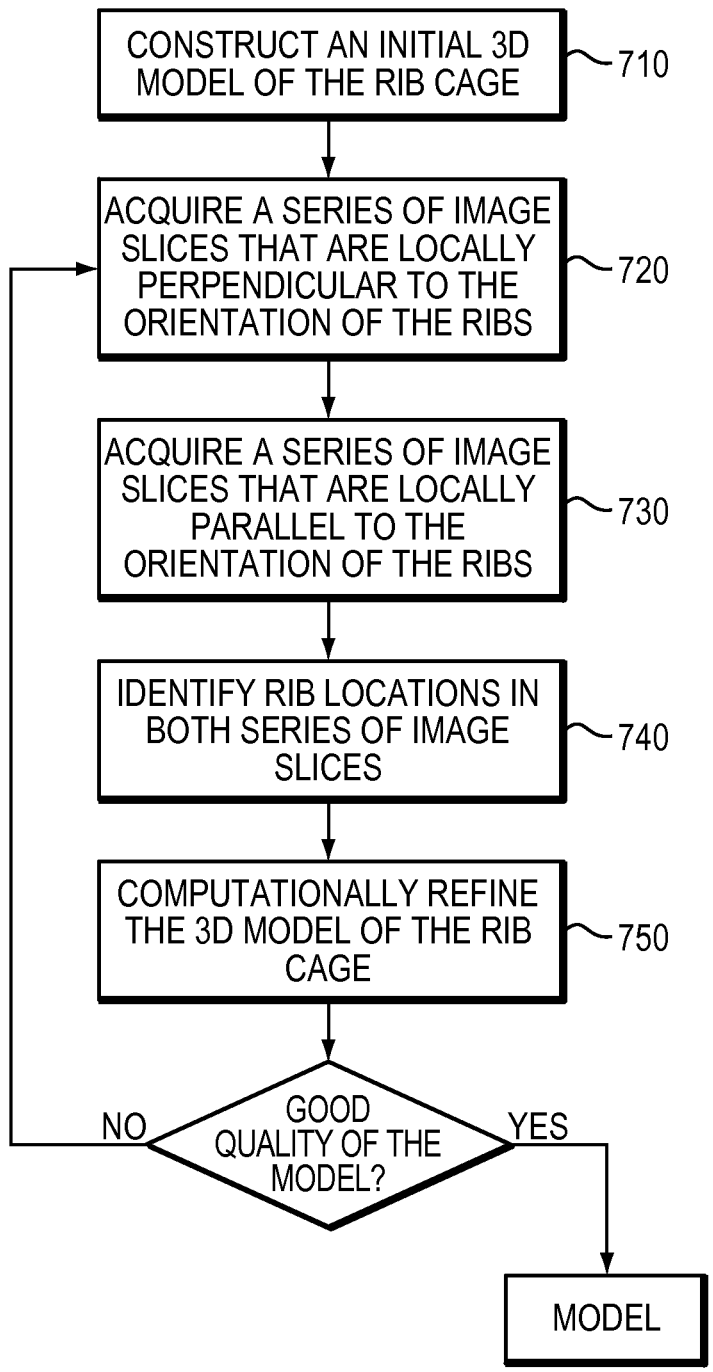
FIG. 7 depicts an iterative process of constructing a three-dimensional model of the rib cage utilizing the image slices.

In order to take image slices locally perpendicular or parallel to the ribs, the specific orientations at the various locations along the ribs should be known, at least approximately, prior to imaging. In some embodiments, this information is calculated from a spatial model of the rib cage. With reference to FIG. 7, an initial model may be created in step 810 based on images obtained, for example, by computed tomography (CT). To facilitate MRI within the reference frame provided by the CT-image-based model, an approximate registration between the CT images and the MR images may be utilized. In steps 720 and 730, two series of image slices (perpendicular and parallel to the local orientation of the ribs) may then be obtained based on the initial rib cage model. The series of image slices generally provides more detailed and accurate information than the initial model built from CT images. Accordingly, after rib locations have been identified in the image slices (step 740), the three-dimensional model of the rib cage may be computationally refined based on the identified rib locations (step 750). The series of image slices may be repeatedly taken until a termination condition is satisfied. For example, the process may be stopped when a convergence criterion is met, i.e., when the changes between successive iterations fall below a threshold at which they are deemed negligible. Alternatively, the process may be terminated after a predefined number of iterations (e.g., two iterations) that experience or simulations have shown to result in a satisfactory quality of the rib cage model.

Figure 8:
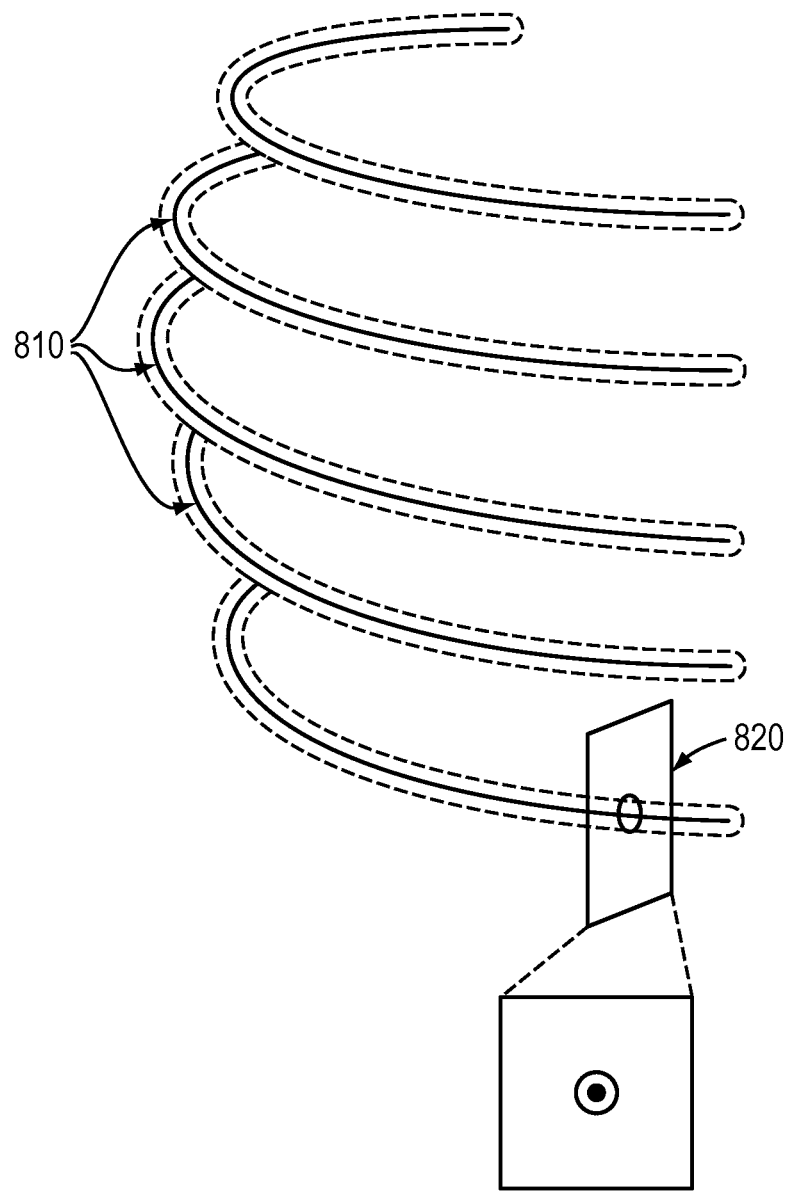
FIG. 8 illustrates each rib modeled as a one-dimensional curved line.
Figure 9:
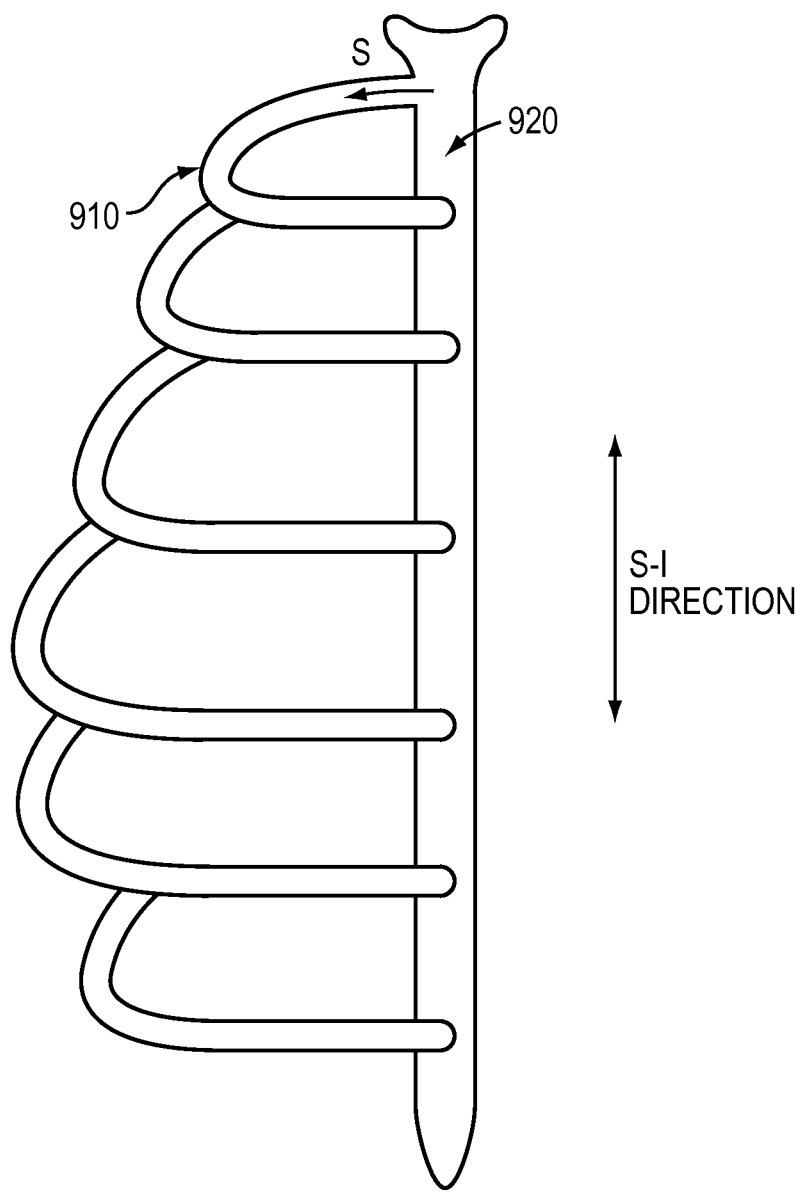
FIG. 9 depicts a single one-dimensional variable describing the length along a rib measured from the spinal cord.

In various embodiments, a spatial three-dimensional model of the rib cage is constructed from one-dimensional "thread" models of the individual ribs in conjunction with ellipses characterizing the cross-sections of the ribs. As described previously, the ellipses model describes the height, width, and angle of the approximately elliptical local cross-sections of the ribs. On the other hand, the threads model is utilized to characterize the locations of the rib curves, i.e., the locations of the cross-section centers. With reference to FIG. 8, each rib is modeled as a one-dimensional curved line 810 generated by moving along the rib at the middle of its cross-section 820. Note that one-dimensional here means that the curved line can be describes as a (multi-valued) function of a single parameter. Denoting the parameter that defines the location along each rib curve with s, the location of the curve (i.e., the center of the cross-section) for each rib, k, is given as: $\{x_k(s), y_k(s), z_k(s)\}$, where x, y, and z are the coordinates in a three-dimensional Cartesian coordinate system. The cross-section characteristics at that location are then given as: $\{h_k(s), w_k(s), a_k(s)\}$, where h, w, and a are the height, width, and angle of the ellipse, respectively. The parameter s can be any geometric variable that has a one-to-one correspondence to the locations along the ribs. Referring to FIG. 9, s may be, for example, the length along the rib 910 measured from, e.g., the spinal cord 920, or the polar angle φ in a spherical coordinate system where the pivotal z-axis is in the vertical (superior-inferior) direction and is located at a central position inside the rib cage (e.g., at half distance between the sternum and the spine). The one-dimensional rib models are related to each other since determination of the orientation and location of one rib practically imposes restrictions on the state of the other ribs since the ribs are all connected.

The image region used to identify the locations of the ribs (threads model) and the shape of the ribs (ellipses model) may be segmented manually and/or automatically by the processor 570 (which, again, may or may not be part of the controller 130) into a series of image slices to construct the model of the rib cage. In some embodiments, modeling is limited to a specific part of the rib cage in which the acoustic energy is applied, for example, for the purpose of liver treatment.

Figure 10A:
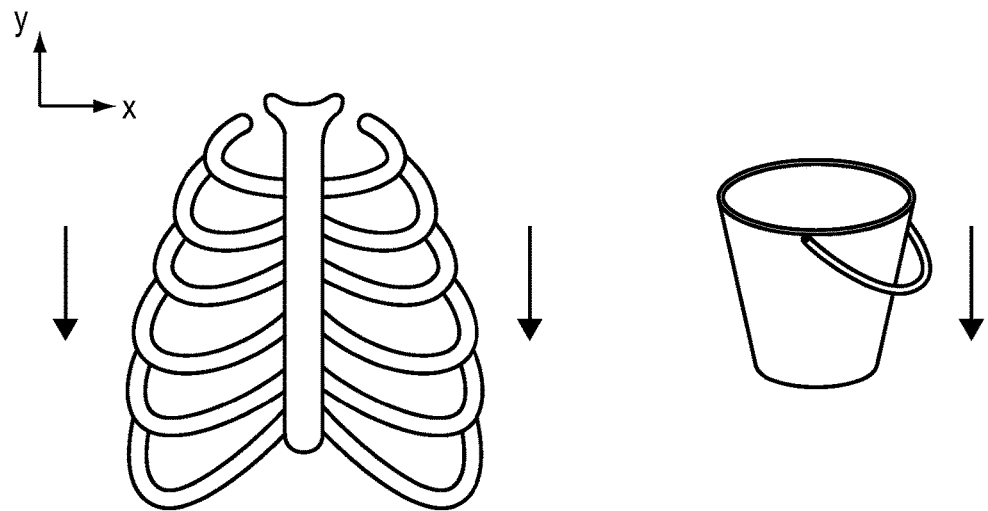
FIG. 10A depicts the movement of the rib cage during expiration in the bucket-handle model.
Figure 10B:
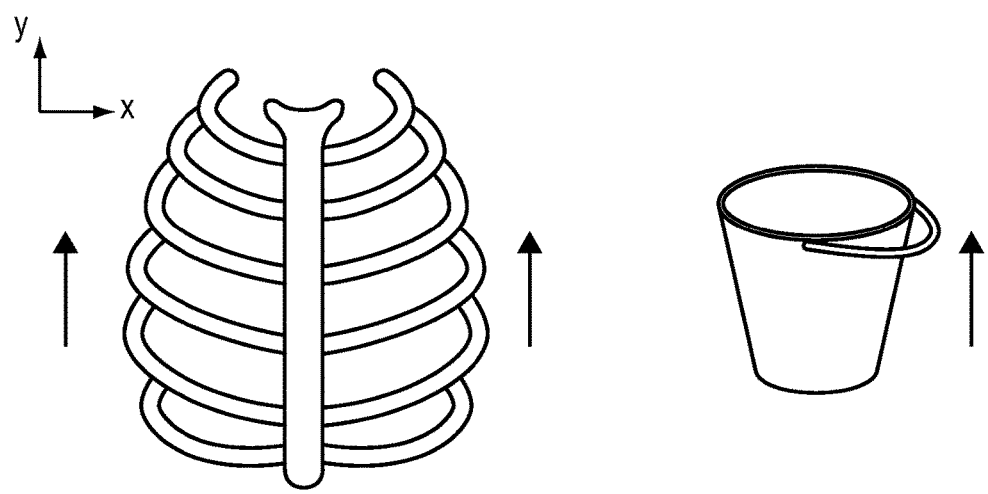
FIG. 10B depicts the movement of rib cage during inspiration in the bucket-handle model.

Breath cycles or non-periodic motions of the patient result in movement of the rib cage. However, a three-dimensional model of the rib cage constructed as explained above only describes one specific stage, e.g., the expiration stage. Without adjusting the model of the rib cage accordingly, the movements may cause serious problems during treatment, e.g., they may result in overheating the ribs. In various embodiments, therefore, rib cage motion is tracked and accounted for. The rib cage, though not rigid, is rather limited in its degrees of freedom; the relevant motion degrees of freedom are limited, especially, if the region of interest is confined to the treatment zone (i.e., a sub-region of the rib cage, such as the liver). Therefore, a simple, e.g., one-dimensional model of rib-cage motion may suffice to define the movement, and rapidly taken perpendicular and/or parallel images may determine the stage of movement at any time of interest with sufficient accuracy. For example, a "bucket-handle" model, as depicted in FIGS. 10A and 10B, may be used to describe the movement of the rib cage during respiration. During expiration (FIG. 10A), the rib cage moves downwards (i.e., in the negative y direction), whereas, during inspiration (FIG. 10B), the ribs rise upwards (i.e., in the positive y direction). These movements perpendicular to the orientation of the ribs (i.e., in the y direction) are relevant to treatment, whereas movement parallel to the orientation of the ribs (e.g., in the x direction) is not.

Figure 11:
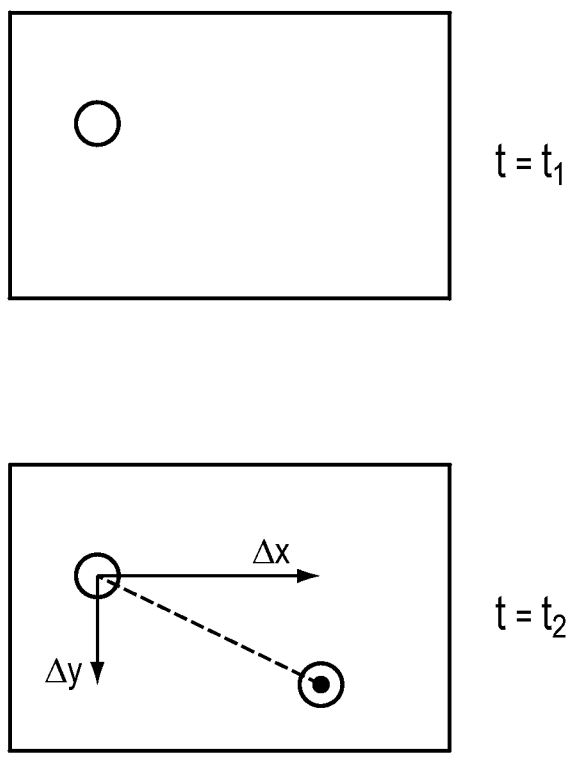
FIG. 11 depicts an in-plane shift of the ribs determined by the two-dimensional coordinates.

Each image slice provides information about two motion values. For example, in a perpendicular image, referring to FIG. 11, the two-dimensional coordinates of an in-plane shift of the ribs, i.e., $\Delta x$ and $\Delta y$, can be determined. Therefore, assuming that the rib cage has N degrees of freedom to move, N/2 image slices should be obtained to model the motion of the rib cage. This indicates that tracking the ribs motion can be achieved by tracking a small number of images. For example, since rib cage motion has only one degree of freedom in the bucket-handle model, a single image would suffice to identify the stage of motion.

Figure 12:
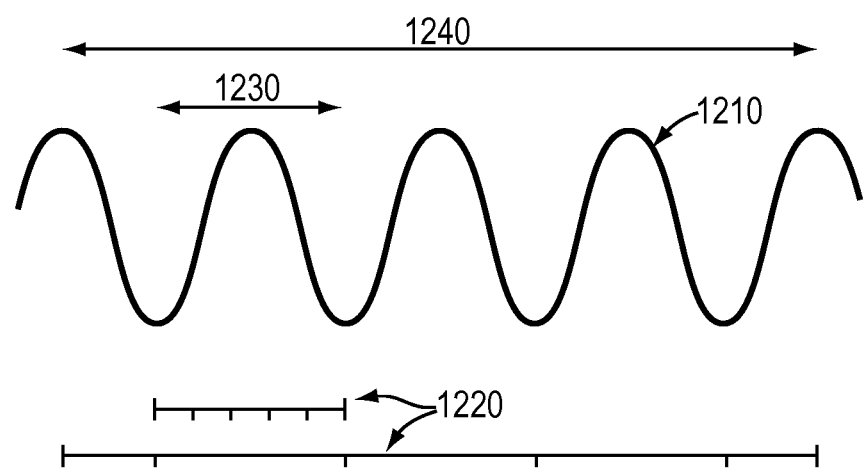
FIG. 12 depicts the breath cycle characterized by a device or tracking the movement of an internal organ.

In some embodiments, the breath stages are determined using a tracking device (such as a belt or navigator) or by image-based tracking of an internal organ (e.g., the liver), and the motion model of the rib cage is created based thereon; the model parameters are stored in nonvolatile memory and the model is implemented by, e.g., the processor 570. Referring to FIG. 12, the breath cycle, as measured by a special device or via organ-tracking in images, may be characterized by a periodic waveform 1210. A small number of image slices 1220 of the rib cage may be taken within one periodic cycle 1430 to construct a set of images that characterizes the rib locations throughout the cycle of motion. Alternatively, the image slices within a cycle may be taken over a few cycles 1440 and correlated to the respective stages of motion based on the information from the tracking device or image-based organ tracking, i.e., the full set can be constructed by gating. This approach reduces the required image update rate. In some embodiments, images are taken at a rate of about 10 images per second.

In general, the MRI methods described above may be carried out using systems such as, for example, the MRg-FUS system described above with reference to FIG. 1A in conjunction with the focused ultrasound system depicted in FIG. 1B, supplemented by computational functionality for analyzing the MR image slices to identify the ribs therein, constructing and/or refining the model of the rib cage based on the images, and, optionally, tracking the motion of the rib cage. Such computational functionality may be implemented in hardware, software, or a combination of the two, which may be integrated in the computation unit 112 of the MRI system or the controller 130 of the ultrasound system, or provided in a separate computing facility (e.g., a suitably programmed general-purpose computer including a processor and memory) in communication with the MRI system and/or the ultrasound system. For embodiments in which the functions are provided as one or more software programs, the programs may be written in any of a number of high level languages.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A method for transcostal ultrasound treatment of target tissue, the method comprising:
   (a) obtaining a generic model of a rib cage, the model comprising a plurality of parameters;
   (b) transmitting ultrasound waves to the target tissue;
   (c) estimating values of the plurality of parameters based on ultrasound reflections;
   (d) determining whether the ultrasound reflections associated with the estimated values of the parameters are maximized; and
   (e) if so, then based on the model of the rib cage and the estimated values of the parameters, treating the target tissue by focusing ultrasound into the target tissue without damaging ribs;
   if not, then,
      (i) updating the values of the parameters based on (A) the ultrasound reflections and (B) the estimated values of the parameters or previously updated values of the parameters;
      (ii) repeating the updating step until the ultrasound reflections associated with the updated values of the parameters are maximized; and
      (iii) based on the model of the rib cage and the updated values of the parameters, treating the target tissue by focusing the ultrasound into the target tissue without damaging the ribs.

2. The method of claim 1, wherein, during the treatment, the ultrasound is focused in a pattern that substantially avoids the ribs.

3. The method of claim 1, wherein transmitting ultrasound waves to the target tissue in step (b) comprises scanning an estimated rib zone with an ultrasound focus and analyzing the ultrasound reflections resulting therefrom.

4. The method of claim 3, wherein analyzing the ultrasound reflections comprises associating the ribs with the ultrasound reflections above a specified intensity threshold.

5. The method of claim 3, wherein a focused-ultrasound pulse energy during scanning is lower than a focused-ultrasound pulse energy during treatment.

6. The method of claim 3, wherein the ultrasound focus is a point focus.

7. The method of claim 3, wherein the ultrasound focus is a line focus.

8. The method of claim 3, wherein multiple portions of the estimated rib zone are scanned in parallel with multiple ultrasound foci.

9. The method of claim 8, wherein the multiple ultrasound foci are generated by multiple sub-arrays of a phased-array ultrasound transducer.

10. The method of claim 1, wherein transmitting ultrasound waves to the target tissue in step (b) comprises irradiating the ribs with the ultrasound waves and, based on the ultrasound reflections resulting therefrom, volumetrically reconstructing a reflected ultrasound field.

11. The method of claim 10, wherein the ultrasound waves are selected from the group consisting of plane waves, omni-directional waves, and focused waves.

12. The method of claim 10, wherein the volumetric reconstruction utilizes at least one of time-of-flight correlation, Raleigh integrals, or Fast Fourier Transform.

13. The method of claim 10, further comprising determining locations of the ribs by associating the ribs with ultrasound field strengths above a specified intensity threshold.

14. The method of claim 1, further comprising tracking rib motion during treatment based, at least in part, on changes in the ultrasound reflections.

15. The method of claim 14, wherein the rib motion tracking is further based on a computational model of the rib motion.

16. The method of claim 1, further comprising validating ultrasound beam apodization prior to treatment based on the ultrasound reflections.

17. A system for transcostal ultrasound treatment of target tissue, the system comprising:
- a transducer array, comprising a plurality of transducer elements, for transmitting acoustic energy to the target tissue and receiving acoustic reflections thereof;
- a processor coupled to the array for:
  - obtaining a generic model of a rib cage, the model comprising a plurality of parameters;
  - estimating values of the plurality of parameters based on the acoustic reflections from the target tissue; and
  - determining whether the acoustic reflections associated with the estimated values of the parameters are maximized;
  - if not, then,
    - (i) updating the values of the parameters based on (a) the acoustic reflections and (b) the estimated values of the parameters or previously updated values of the parameters; and
    - (ii) repeating the updating step until the acoustic reflections associated with the updated values of the parameters are maximized; and
- a controller for driving the transducer elements to acoustically treat the target tissue based at least in part on the model of the rib cage and the estimated values or updated values of the parameters whose associated acoustic reflections are maximized.

* * * * *